(12) United States Patent
Bychkov et al.

(10) Patent No.: US 12,308,117 B2
(45) Date of Patent: May 20, 2025

(54) METHOD FOR UPDATING A VENTILATOR (71) Applicant: Loewenstein Medical Technology S.A., Luxembourg (LU)

(72) Inventors: Igor Bychkov, Ettlingen (DE); Maria Kopaigorenko, Karlsruhe (DE); Matthias Schwaibold, Karlsruhe (DE); Benjamin Born, Karlsruhe (DE); Patrick Eisenreich, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 531 days.

(21) Appl. No.: 17/449,478

(22) Filed: Sep. 30, 2021

(65) Prior Publication Data
US 2022/0108794 A1   Apr. 7, 2022

(30) Foreign Application Priority Data
Oct. 2, 2020   (DE) .......................... 102020006038.2

(51) Int. Cl.
G06F 8/65 (2018.01)
G16H 40/40 (2018.01)
H04L 67/00 (2022.01)
H04L 67/125 (2022.01)

(52) U.S. Cl.
CPC .............. *G16H 40/40* (2018.01); *G06F 8/65* (2013.01); *H04L 67/125* (2013.01); *H04L 67/34* (2013.01)

(58) Field of Classification Search
None
See application file for complete search history.

(56) References Cited

U.S. PATENT DOCUMENTS

| | | | |
|---|---|---|---|
| 8,516,121 B1 * | 8/2013 | Telang | H04L 41/0896 709/212 |
| 11,042,606 B2 * | 6/2021 | Trull | G06F 17/40 |
| 2005/0257214 A1 | 11/2005 | Moshir et al. | |
| 2011/0073107 A1 | 3/2011 | Rodman et al. | |
| 2012/0266251 A1 | 10/2012 | Birthwhistle et al. | |
| 2013/0104120 A1 * | 4/2013 | Arrizza | A61M 5/142 717/173 |
| 2014/0281015 A1 * | 9/2014 | Orona | H04L 67/12 709/232 |

(Continued)

FOREIGN PATENT DOCUMENTS

JP   2019535060 A   12/2019

OTHER PUBLICATIONS

Günter Born, "Windows 8-Falle: Hoher Datendurchsatz bei 3G-Verbindungen | Borns IT- und Windows-Blog". (Feb. 15, 2013), pp. 1-4, URL: https://www.borncity.com/blog/2013/02/15/windows-8-falle-hoher-datendurchsatz-bei-3g-verbindungen/, (Feb. 11, 2022), XP055890624 [Y] 15 * pp. 1-4.

Primary Examiner — Marina Lee
(74) Attorney, Agent, or Firm — Abel Schillinger, LLP (57) ABSTRACT A method for updating the firmware and software of a ventilator, wherein the firmware and the software of the ventilator are divided into individual modules and separate updates are provided for each module in the form of module updates and these module updates are transferred to the ventilator from at least one remote station spatially separated from the ventilator via at least one interface of the ventilator and the module updates are performed on the ventilator.

20 Claims, 1 Drawing Sheet (56) References Cited

U.S. PATENT DOCUMENTS

| | | | |
|---|---|---|---|
| 2015/0070187 A1* | 3/2015 | Wiesner | G16H 40/67 340/870.02 |
| 2016/0196132 A1* | 7/2016 | Searle | G06F 8/65 717/173 |
| 2018/0074808 A1 | 3/2018 | O'Connor et al. | |
| 2018/0247353 A1* | 8/2018 | Al-Ali | A61B 5/0205 |
| 2018/0285094 A1* | 10/2018 | Housel | G06F 8/65 |
| 2022/0084671 A1* | 3/2022 | Schwaibold | G16H 40/40 |

* cited by examiner

METHOD FOR UPDATING A VENTILATOR

CROSS-REFERENCE TO RELATED APPLICATIONS

The present application claims priority under 35 U.S.C. § 119 of German Patent Application No. 102020006038.2, filed Oct. 2, 2020, the entire disclosure of which is expressly incorporated by reference herein.

BACKGROUND OF THE INVENTION

1. Field of the Invention

The invention relates to a method for updating a ventilator.

2. Discussion of Background Information

Modern ventilators have a large number of built-in electronic components, many of which are programmable and operated via firmware and software. From time to time, new functions are developed for these components or bugs in the original programming are corrected. In order to transfer these changes to existing ventilators, the firmware and software of the ventilators must be updated.

Often, the firmware and software of the prior-art ventilators are updated as a whole with a major update or the ventilator is completely re-loaded with a new firmware and software version. The transfer and installation of such updates consumes a large amount of resources, including taking a long time. If the transfer is interrupted unintentionally, it can cause parts of the update that have already been transferred to be completely lost and require retransmission, which further delays the updating process.

In view of the foregoing, it would be advantageous to have available a method for reliably operating a ventilator.

SUMMARY OF THE INVENTION

The present invention provides a method for updating the firmware and software of a ventilator. According to the method, the firmware and the software of the ventilator are divided into individual modules and separate updates can be provided for each module in the form of module updates and these module updates can be transferred to the ventilator from at least one remote station spatially separated from the ventilator via at least one interface of the ventilator and the module updates can be performed on the ventilator.

In some embodiments of the method the module updates are each divided into data packets which are transferred to the ventilator via an interface of the ventilator and stored, wherein after the transfer of all data packets of a module update the data packets are assembled and the respective module update is performed.

In some embodiments of the method, the data packets of a module update are stored on the ventilator even after the data transfer is interrupted.

In some embodiments of the method, the transfer of the data packets is resumed after an interruption to the data transfer.

In some embodiments of the method, the transfer of the data packets is resumed after an interruption to the data transfer, wherein the transfer is restarted with the last data packet that was started but not completely transferred.

In some embodiments of the method, the data packets of a module update are stored on the ventilator until the module update has been performed or until a command to delete the data packets is issued.

In some embodiments of the method, the transferred data packets on the ventilator of an incompletely transferred module update are discarded/deleted and the missing data packets are not transferred if a more recent version of the module update is available, in which case the data packets of the new version of the module update are then transferred.

In some embodiments of the method, a message about the status of the module update is generated and/or issued by the ventilator and/or the spatially separated remote station.

In some embodiments of the method, the transfer and/or execution of the module update must be requested or confirmed on the ventilator and/or the spatially separated remote station.

In some embodiments of the method, the transfer of the module update or data packets is suspended under certain conditions.

In some embodiments of the method, the transfer of medical, patient-specific and/or treatment-related data is prioritized over the transfer of data packets of the module updates.

In some embodiments of the method, the priority of the transfer can be individually adjusted on the ventilator and/or on the spatially separated remote station for individual data types (e.g. medical, patient-specific and/or treatment-related data; module updates).

In some embodiments of the method, the transfer and execution of a module update is preferred over all other data transfers under certain circumstances.

In some embodiments of the method, the module updates are divided into data packets and the maximum size of the data packets is from 100 kilobytes to 100,000 kilobytes. In some embodiments, the maximum size of the data packets is between 100 kilobytes and 1000 kilobytes.

In some embodiments of the method, when a newer version of the module update is available a check is first made as to whether one of the previous module updates is necessary in order for the new version of the module update to be performed, in which case the older version of the module update is then transferred and performed before transferring and performing the newer version of the module update.

In some embodiments of the method, if a plurality of module updates for different modules is available, the module updates are transferred and performed consecutively, wherein the next module update is only transferred and performed if the previous module update is fully completed.

In some embodiments of the method, if a plurality of module updates for different modules is available, the module updates are transferred and installed at the same time.

In some embodiments of the method, if a plurality of module updates for different modules is available, the module updates are transferred and performed consecutively, wherein the process starts with the transfer of the next module update after the transfer of the previous module update is completed and without waiting for the successful execution of this previous module update.

In some embodiments of the method the transfer of the module update is automatically interrupted by the ventilator based on the connection between the ventilator and the spatially separated remote station.

In some embodiments of the method, if the ventilator and the remote station are connected via a mobile radio connection (LTE, 3G, etc.) the transfer of the module update does not take place and is interrupted if the connection between the ventilator and the spatially separated remote station is switched to such a mobile radio connection.

The ventilation system provided by the invention comprises at least one ventilator (1) and a spatially separated remote station (10), wherein the firmware and the software of the ventilator (1) are divided into individual modules (20, 30, 40, 50, 60, 70, 80, 90) and separate updates are provided for each module (20, 30, 40, 50, 60, 70, 80, 90) in the form of module updates, and these module updates are transferred to the ventilator (1) from the remote station (10) via at least one interface of the ventilator (1) and the module updates are performed on the ventilator (1).

It should be noted that the features listed individually in the claims can be combined with each other in any technically appropriate way and specify additional embodiments of the invention. The description additionally characterizes and specifies the invention, in particular in relation to the FIGURES.

It should also be pointed out that a conjunction "and/or" as used herein, placed between two features and linking them together, is always to be interpreted such that in a first embodiment of the subject matter according to the invention only the first feature can be present, in a second embodiment only the second feature can be present and in a third embodiment both the first and the second feature can be present.

For the purposes of the invention, a ventilator means any device that can be used for medical purposes. These medical purposes can be, for example, the treatment of a patient, the diagnosis of diseases and ailments of a patient, or even providing life-support functions. In particular, ventilators can be understood in the form of ventilators and diagnostic devices. Diagnostic devices can generally be used to acquire medical parameters of a patient. They also include devices that can acquire and optionally process medical parameters of patients in combination with or exclusively relating to respiration. A ventilator means any device that assists a user or patient in natural breathing, performs respiration for the user or patient, and/or is used for respiratory treatment and/or otherwise influences the breathing of the user or patient. This includes, for example, but not exhaustively, CPAP and BiPAP devices, narcosis or anesthesia devices, respiratory treatment devices, (hospital-based, out-of-hospital or emergency) ventilators, high-flow therapy devices, and cough machines.

An interface is to be understood in the broadest sense to mean any type of device for connecting—regardless of the connection type—between the ventilator and a remote station or a person. For example, an interface for connecting the ventilator to a person can be a user interface that allows the person to interact with the ventilator directly on the ventilator.

The individual components of the ventilator are in modules, wherein the entire ventilator can also be understood as a single module. The definition of a module can be made from various points of view, which will not be explained further here and has no influence on the invention as such. It is also possible for different modules to overlap using the components of the ventilator. For example, a component can be assigned to two modules. In addition, the individual modules can also be combined into module groups, although these module groups may also overlap under certain circumstances.

If in some embodiments a module update is not fully transferred, it must first be checked whether a more recent module update is available. If a more recent module update is available, it must be determined whether the new module update is strictly dependent on the previous update or can be installed independently (across versions). If the module update is based upon the previous version, then the previous version must be transferred and installed first. If this is not the case, the data from the incomplete module update can be deleted and the transfer of the new module update can be started.

In some embodiments of the method, the transfer of the module update is suspended or postponed if another data transfer is currently planned. This is important, for example, in the case of mobile radio connections, as these are often expensive, weak and/or volume-limited. The importance of the module update can therefore be considered to be of secondary importance. In some cases, the transfer of module updates over a mobile radio connection may also be completely prohibited.

Occasionally, important updates may be provided, for example to close security loopholes. For example, these can be indicated as important by the server, so that the ventilator receives a command, for example, which contains information that the module update should be transferred and installed immediately. In some embodiments this can also be classified as being so important that without the corresponding module update the operation of the ventilator is no longer possible.

For example, the firmware of the ventilator is divided into individual modules, each of which can be updated individually by newer versions of the firmware. The modularity of the firmware makes it possible to transfer only the new firmware of a single module. This reduces the size of the updates and potentially allows for faster deployment of updates to individual modules rather than providing a major update to the entire firmware.

For example, the new version of the respective module firmware is divided in turn into a plurality of smaller data packets, which are transferred to the ventilator and (temporarily) stored there. If the transfer is interrupted, the transfer of the missing packets can be resumed at a later time. Once all the packets in an update are transferred, they are assembled into the complete module update and the device can perform the update.

For example, if no connection can be made to the ventilator for a considerable period of time, it may be the case that a newer version of the module update than the one that has not yet been fully transferred has been provided in the meantime. If this is the case, the already transferred packets of the not yet fully transferred version can be discarded and the transfer of the packets of the new version can be started. If the newer version of the module update is based upon the older version, i.e. is dependent on it, the older version can also be transferred and performed first and then the update is continued with the new version.

In some embodiments of the method, the current bandwidth and/or stability of the interface is checked before the module is updated. This is particularly true for mobile radio connections. For example, the update will only be performed or continued if the bandwidth and/or stability of the connection between the ventilator and the remote station exceeds a minimum value.

For each module, in some embodiments a priority is assigned for updating the firmware and/or software. For example, it can be made dependent on the size of the update file or the relevance of errors to be corrected by the update or of new features. For example, the priority can also be based on logical dependencies between the individual modules, for example, if the updated version of a module can only be executed on the condition that another module has been previously updated. All modules are then updated in the order of priority. If the bandwidth is low and/or the connection is unstable, the modules with a high priority are the first or only ones to be transferred.

In some embodiments of the method, the division of the entire firmware and/or software into modules can reflect the modularization of the hardware. In this case, one firmware/software module is created per programmable electronic component, e.g. microprocessor, radio module, memory module, interface module, sensor module etc. and at least optionally, updated individually. For example, the division can also take place within an electronic component, e.g. in at least one operating system module and at least one application module which the operating system module requires in order to be able to run. In addition to at least one application module, at least one separate language module can exist, in which characters and/or display texts are stored.

In some embodiments the updating is only carried out during suitable operating states of the ventilator, e.g. not during active therapy or diagnostic functions.

In some embodiments a command/instruction can also be sent to the ventilator via the interface, which permits further use only after the completion of an update, in particular if the initial version of the ventilator or the module firmware/module software contains critical errors.

The version to which the individual modules are updated can be selected, for example, based on the location of the ventilator, in particular the country. The selection can be made in particular on the basis of the approval situation in the country concerned. In particular, the latest approved version in the country concerned is offered or recommended for the update. The location can be ascertained, for example, by means of GPS, IP address, mobile network operator or dial-up cell in a mobile radio network, language selection, or by user input.

In some embodiments, the ventilator transfers its electronic and/or mechanical configuration prior to performing the update, e.g. the presence or version of interface or sensor modules or other essential components. Based on the configuration, the required modules and their versions are selected for the update.

In some embodiments, the updating of the firmware and/or software must be additionally confirmed on the ventilator. For example, it is thus possible to prevent a specially adapted firmware or software from being overwritten by a general update and becoming unusable.

In some embodiments, the validity of module updates and/or individual data packets is checked. For example, a module update and/or data packet may be invalid if no or another update is requested and/or a checksum is not correct, and/or the encryption of the data is incorrect or missing and/or a signature of the data is missing or incorrect.

In some embodiments, provision may be made first to check the validity of the individual data packets after they are transferred to the ventilator. For example, the check is performed to determine whether an error-free transfer has taken place. It can also be checked whether the transferred data packet actually belongs to the module and/or the module update and/or the version to be installed. Such a check can be carried out, for example, by means of a checksum or similar tests.

It may also be provided that after all data packets have been received, the data packets are assembled, for example in the memory of the device. After assembling the data packets for the module update, a further check can be carried out, for example for completeness, validity, and/or to determine whether the module update matches the module. Only if this check is successful will the module update be installed. An installation can include, for example, loading the program code into the program memory and then activating it.

In some embodiments, the data packets are encrypted and/or digitally signed during or before the transfer. It can also be provided that the entire module update is encrypted and/or digitally signed. If the module update and/or the individual data packets are digitally signed, only those data packets/module updates that have a valid signature are accepted and/or installed by the ventilator. The same applies to the encryption of module updates, which are only activated or installed if a valid key is present.

BRIEF DESCRIPTION OF THE DRAWING

An exemplary embodiment of the method according to the invention is described in more detail by reference to the only FIGURE, which schematically shows a ventilator, the firmware and software of which are divided into different modules, as well as the spatially separated remote station.

DETAILED DESCRIPTION OF EXEMPLARY EMBODIMENT

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawing making apparent to those of skill in the art how the several forms of the present invention may be embodied in practice.

Figure 1:
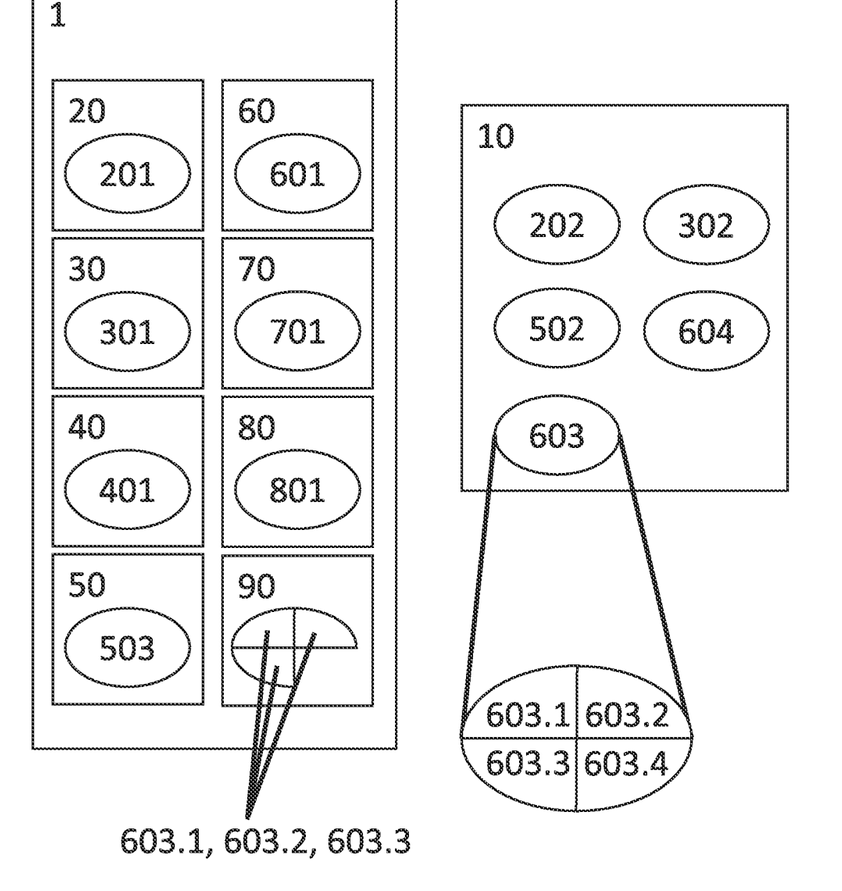

The FIGURE shows a ventilator 1, the firmware and software of which are divided into different modules, as well as the spatially separated remote station 10. By way of example, the ventilator 1 is assigned a sensor module 20, a conditioning module 30, a detection module 40, a control module 50, a communication module 60, a monitoring module 70, a software module 80, and a memory module 90. The modularization of the firmware and software can be based, for example, on the modularization of the hardware. For example, each hardware module is assigned a corresponding firmware and/or software module. It is also conceivable that a subdivision is made based on electronic components, so that each electronic component is divided into, for example, an operating system module and an application module. For example, it can be configured such that the application module requires the operating system module in order to be executed.

The sensor module 20 is configured to collect measurements, in particular of parameters related to respiration air-flow, respiration volume, respiration rate, duration of inhalation and exhalation, respiration contour, leakage or therapy pressure. Optionally, the sensor module 20 can make additional measurements of components or temperature of the respiratory gas or the blood. The sensor module 20 transmits the measurements to the conditioning module 30.

The conditioning module 30 can prepare the measurements. For example, the conditioning module 30 can perform smoothing, artifact cleaning, or down-sampling of the measurements. In some embodiments the conditioning module 30 is also designed as a combined conditioning and calculation module, alternatively or additionally these modules can also be designed as separate modules. From the measured values acquired by the sensor module and prepared by the conditioning module, the calculation module calculates signals and/or characteristic parameters, such as a mean value, a median, a percentile, a derivative, a frequency distribution, a duration or proportion of threshold values being exceeded or undershot.

The detection module 40 is configured to detect events/conditions such as alarms, breathing interruptions, artifacts, coughing fits, oxygen (de-)saturation levels, asynchronously between the device and user, inhalation, exhalation or mandatory breaths.

The control module 50 is used, for example, to control the ventilator 1, in particular a blower and/or valve module, not shown here, for generating the respiratory gas flow or ventilation pressure. Also, the control module 50 may be designed to control other components and/or modules of the ventilator 1. In some embodiments, the control module 50 can also be further divided and consist of a plurality of control modules, each of which controls an individual module and/or component of the ventilator 1.

The communication module 60 is configured in such a way that the ventilator 1 can use it to connect to spatially separated remote stations, such as a server, and exchange data with this remote station, i.e. receive data from the remote station and send data to the remote station. The communication module 60 acts as an interface to the remote station 10, among other things. For example, the communication module 60 is designed and configured as an interface for the following communication systems: GSM, Lora, LPWAN, NB-IOT, LTE-M, LTE, UMTS, LAMN WiFi, WLAN, Bluetooth, LAN, WPAN. In addition, the communication module 60 can also act as an interface for wired data connections or for data storage devices such as USB sticks and SD cards.

The monitoring module 70 detects technical problems with the ventilator 1, for example. Technical problems can include a low battery level, faults in the electronics, a defective battery, a defective component, a power failure, an incorrectly functioning accessory, an implausible measurement, or a departure from a permitted temperature range. The monitoring module 70 can display or transmit an alarm on the ventilator 1 via an interface if a technical problem is detected.

The memory module 90 stores, or at least buffers, the values/parameters acquired by the sensor module 20 and/or the values, data and/or information prepared by the conditioning module 30, inter alia. For example, buffering means that the values, data, and/or information are stored until a transfer is made and then, for example, deleted or enabled for overwriting. If module updates are transferred to the ventilator 1, they are at least buffered in the memory module 90.

The remote station 10 can be any data source spatially separated from the ventilator 1, such as a server to which the communication module 60 can establish a connection. However, the remote station 10 can also be a USB stick or an SD card or another storage medium, for example. For example, a smartphone and/or other Bluetooth-enabled medium can also be considered as the remote station 10.

Each module is assigned a set of firmware and/or software. For example, the respective firmware and/or software versions are identified by the three-digit designation numbers. The first two digits represent the module to which the firmware and/or software version belongs, and the third digit indicates an exemplary version number, wherein a higher number indicates a more recent version. Thus, the sensor firmware 201 and 202 must be assigned to the sensor module. The sensor firmware 202 is the more recent version of the firmware relative to the sensor firmware 201. For reasons of transparency, no firmware has been assigned to the memory module 90, the data packets 603.1, 603.2 and 603.3 are assigned to the memory module 90, which is intended to represent an example of storage of the data packets in the memory module 90.

For example, updates for the firmware and/or software are provided via the remote station 10 and transferred via the interface/interfaces of the communication module 60 to the ventilator 1, or to the memory module 90 of the ventilator 1 as appropriate.

In the example situation illustrated in the FIGURE, module updates are provided via the remote station 10 for the sensor module 20, the conditioning module 30, the control module 50 and for the communication module 60. The sensor firmware 201 is currently installed for the sensor module 20 of the ventilator 1, and the newer sensor firmware 202 is provided by the remote station 10 as a module update. The conditioning module 30 runs with the conditioning firmware 301 and the remote station also provides a newer conditioning firmware 302 for this module. In addition, the control firmware 503 is installed for the control module 50; the remote station 10 here provides the older control firmware 502. In addition, the remote station 10 also provides the communication firmware 603 and 604 for the communication module 60, wherein the older communication firmware 601 is installed on the ventilator 1.

If a connection is established between the remote station 10 and the ventilator 1, it is first checked, inter alia, which firmware version is installed on the ventilator 1. For example, the test can be performed by the remote station 10, for example, by the ventilator 1 sending information about the installed firmware to the remote station 10 and the remote station 10 verifying whether more recent versions of the firmware are available in the form of a module update. In some embodiments, the ventilator 1 can also check whether more recent versions of the firmware are available. For this purpose, the remote station 10 sends information about the available firmware and the ventilator 1 matches this against the installed firmware, for example. If the remote station is an SD card or a USB stick, for example, the ventilator 1 can also check the contents of the SD card for module updates, i.e. more recent firmware.

In addition, for example, the available/current bandwidth (transmission speed) and the stability of the connection are also checked before transmission and execution of the module update. This is particularly true for mobile radio connections. This ensures, for example, that no malfunctions occur during the transfer or whether the bandwidth/transmission speed is sufficient to transmit both treatment-related/medical data and settings between remote station 10 and ventilator 1 and to transfer the necessary data for the module update. For example, also during transmission or execution of the module update, the connection to the remote station 10 is checked and only continued if the stability and/or the bandwidth exceeds a minimum value.

If module updates are available or provided by the remote station 10, the respective module update is transferred to the ventilator 1 and at least buffered in the memory module 90, for example. If the module update is fully transferred to the ventilator 1, then it can be installed, i.e. the update can be performed.

In the example case illustrated in the FIGURE, the respective module updates for at least the sensor module 20 and the conditioning module 30 would be transferred and performed, so that after the update is complete, the sensor firmware 202 and the processing firmware 302 are installed on the ventilator 1. No module update is transmitted and performed for the control module 50 because a more recent control firmware 503 is already installed and the remote station 10 only provides the older control firmware 502. For example, this can occur if the ventilator 1 has previously received a module update for the control module 50 via an internet connection and is now due to be updated via, for example, an SD card which contains only the older control firmware 502.

For example, the module updates are transferred consecutively, which means that one module update is first transferred completely before the next module update is transmitted. For example, if more than one module update is available, it can be decided which one to transfer first based on a priority of the module update. For example, if the sensor firmware 202 is prioritized over the conditioning firmware 302, the module update to the sensor firmware 202 is transferred to the ventilator first. In some embodiments the transmission of the conditioning firmware 302 is delayed until the module update to sensor firmware 202 is completed. However, it may also be possible that the transfer of the next module update will begin as soon as the transfer of the next module has been completed and, for example, is currently in progress. In some embodiments, it may also be possible for all module updates to be transferred at the same time. It is also entirely possible to install the module updates at the same time.

Whether a module update is transmitted and performed/installed may in some embodiments depend, for example, on the available resources such as memory space in the memory module 90, available processor power, ongoing therapy/diagnosis, data connection, battery level or power supply and/or other data transmissions in progress. For example, a module update can be suspended or postponed if the memory module 90 does not have enough memory to be able to store the module update. In particular during ongoing treatment with the ventilator 1 it may be possible that absolutely no module updates are performed. On the one hand, it could be possible that the processor becomes overloaded during the performance of the update and thus the ventilator 1 will fail, or that an active and/or necessary module for the therapy should be updated which might be unavailable for a short time during the update and would therefore interfere with the therapy.

In some embodiments, the module updates can be deferred, for example when treatment-related or patient-specific data is currently being transferred. A transmission of the module update can also be suspended and/or interrupted if the ventilator 1 is connected to the remote station 10 via a mobile radio connection (LTE, 3G, EDGE, etc.) and/or the existing transmission speed is low or fully utilized.

For example, a priority can be assigned to the module updates. For example, the priority can be based on the size of the file of the module update or else on the relevance of errors to be corrected and/or new functions. For example, in some cases, the priority of the module update may also follow a logical sequence, for example, if the (updated) firmware of a module is only executable if other modules have been previously updated. The transmission and installation/performance of the module update is carried out in the order of priority. For example, if the stability and/or transmission speed of the connection between ventilator 1 and remote station 10 is poor, then high-priority module updates are transmitted and performed first, for example.

In some embodiments, for example, a user interface not shown in the FIGURE can be used to decide whether and which of the available module updates should be transferred and performed/installed. It is also possible to decide manually on the ventilator 1 or via the remote station 10 whether and which module updates should be given preference. In some embodiments, this also allows the module updates to be prioritized over treatment- or patient-related and medical data during the data transfer. In some embodiments an automatic module update is also possible, which can be activated and deactivated on the ventilator 1. When automatic module updating is active, the module updates are automatically transferred to the ventilator 1 and executed/installed, if available.

In addition, for some embodiments of the method, it is conceivable that certain module updates may also take precedence over the therapy itself. This means that in these cases, a therapy session cannot be started before the module update is transferred and installed. For example, these module updates may include bug fixes that affect the safe and proper operation of the ventilator. For example, if errors and/or malfunctions of the firmware and/or software are subsequently detected, which can lead to a malfunction of the ventilator 1 or at least one of the modules, it can be decided that this error correction should be installed as a priority, i.e. with high or highest priority, as a module update. Module updates intended to increase data security, for example to close a security loophole, can also be assigned a particularly high priority, for example the highest priority.

In some exemplary embodiments the module updates are divided into smaller data packets, as shown schematically in FIG. 1 for the communication firmware 601, 603, 604 of the communication module 60. As an example, the FIGURE shows the module update for the communication firmware 603 divided into four individual data packets 603.1, 603.2, 603.3, 603.4. These data packets 603.1, 603.2, 603.3, 603.4 are transferred individually and, after successful transfer of all data packets, are assembled in the ventilator 1 to update the module. The size of the data packets into which a module update can be divided can be set variably. For example, the maximum size of a data packet can be between 100 kilobytes and 100,000 kilobytes, preferably between 100 kilobytes and 10,000 kilobytes or between 100 kilobytes and 1,000 kilobytes. For example, if few or poor data connections are expected, a smaller maximum size can be chosen so that a module update is divided into many small data packets. For example, to minimize the processor load when assembling the data packets for the module update, the size of the data packets can also be larger, i.e. up to 100,000 kilobytes, in order to obtain fewer data packets.

The FIGURE shows an example of the communication firmware 601 installed for the communication module 60. For example, the transfer of the module update to communication firmware 603 has already been started, but up to now only the data packets 603.1, 603.2 and 603.3 have been transferred and stored in the memory module 90. The last data packet 603.4 has not yet been transferred or not completely transferred, so the module update is not yet completely transferred and cannot be performed/installed. If at least the missing data packet 603.4 is made available during the next connection of the ventilator 1 to a remote station 10, this packet can be transferred and the data packets can be assembled for the module update to communication firmware 603. The individual data packets remain in the memory module 90 until, for example, the update process is fully completed and/or an explicit command is issued to delete the data packets. For example, after termination or interruption of the connection or the data transfer between ventilator 1 and remote station 10 the data packets 603.1, 603.2, and 603.3 are not deleted, but instead remain stored.

As an example, the remote station 10 in the FIGURE also provides the more recent version of the communication firmware 604. If the installation of the previous version 603 is not necessary in order that the more recent communication firmware 604 can work, the missing data packet 603.4 of the module update to communication firmware 603 is not transferred when the remote station 10 and ventilator 1 are connected, and the already transmitted data packets 603.1, 603.2 and 603.3 are deleted from the memory module 90 of the ventilator 1. Instead, the module update to communication firmware 604 or the corresponding data packets is/are transferred to the ventilator and the module update is performed/installed.

On the other hand, if, for example, the module update to communication firmware 603 is necessary in order that the communication firmware 604 for the communication module 60 can also be installed in a functional state, then the communication firmware 603 is completely transferred and installed first. Only after successful installation of the module update to communication firmware 603 will the transfer of the module update to communication firmware 604 be started. If this transfer were to be interrupted and the module update not completely transferred and installed and a more recent version of the communication firmware 604 is made available during the next connection, it is checked once again whether the more recent communication firmware depends on one of the previous versions or on the previous version, i.e., whether one of the previous versions of the communication firmware is necessary. If appropriate, the required older version is accordingly transferred and installed first before the newer version is transferred and installed.

For example, which module updates are performed and which version is applied to the ventilator 1 can also be made dependent on the location of the device. The location can be ascertained, for example, by means of GPS, IP address, mobile network operator or dial-up cell in a mobile radio network, language selection, and/or by user input.

In some embodiments of the method, the entire update process can be divided into 2 phases: a phase in which the module updates are transferred to the ventilator and a phase in which the module update is completely transferred and performed/installed. While the first phase of the transfer of the module updates can generally be interrupted, an interruption in the second phase, the installation phase, is not always possible. For example, it may be configured such that high-priority or highest-priority module updates cannot be interrupted. For example, in some embodiments, it can also be configured such that a copy of the current module firmware is stored in the memory module 90 until the new version of the firmware is successfully installed. If the installation of the new firmware were interrupted and therefore the module firmware become no longer functional, the old version could then be reactivated automatically or manually. In some cases, the module update restarts automatically after an interruption, for example the next time the ventilator is switched on. Alternatively or in addition, a module update or the installation can also be prevented, for example, if there is a risk that the module update cannot be successfully completed. This may be the case, for example, if the battery level is too low, so that the ventilator could no longer be supplied with power before the installation is completed.

For example, the ventilator 1 and/or the remote station 10 is/are also configured to generate and/or display information about the status of the module update, such as the number of data packets already transferred, amount of data, module version, progress of the installation. The displays can be in graphical form (e.g. as a progress bar) or also in alphanumeric form.

To sum up, the present invention provides:
1. A method for updating the firmware and software of a ventilator, wherein the method comprises dividing the firmware and the software of the ventilator into individual modules and separate updates are provided for each module in the form of module updates and these module updates are transferred to the ventilator from at least one remote station spatially separated from the ventilator via at least one interface of the ventilator and the module updates are performed on the ventilator.
2. The method of item 1, wherein the module updates are each divided into data packets which are transferred to the ventilator via an interface of the ventilator and stored, and wherein after a transfer of all data packets of a module update the data packets are assembled and the respective module update is performed.
3. The method of any one of the preceding items, wherein the data packets of a module update are stored on the ventilator even after an interruption to the data transfer.
4. The method of any one of the preceding items, wherein a transfer of the data packets is resumed after an interruption to the data transfer.
5. The method of any one of the preceding items, wherein a transfer of the data packets is resumed after an interruption to the data transfer, the transfer being restarted with the last data packet that was started but not completely transferred.
6. The method of any one of the preceding items, wherein the data packets of a module update are stored on the ventilator until the module update has been performed or until a command to delete the data packets is issued.
7. The method of any one of the preceding items, wherein the transferred data packets on the ventilator of an incompletely transferred module update are discarded/deleted and the missing data packets are not transferred if a more recent version of the module update is available, in which case the data packets of the new version of the module update are then transferred.
8. The method of any one of the preceding items, wherein a message about the status of the module update is generated and/or issued by the ventilator and/or the spatially separated remote station.
9. The method of any one of the preceding items, wherein the transfer and/or execution of the module update must be requested or confirmed on the ventilator and/or the spatially separated remote station.
10. The method of any one of the preceding items, wherein the transfer of the module update or the data packets is suspended under certain conditions.
11. The method of any one of the preceding items, wherein the transfer of medical, patient-specific and/or treatment-related data is prioritized over the transfer of data packets of the module updates.
12. The method of any one of the preceding items, wherein the priority of the transfer can be individually adjusted on the ventilator and/or on the spatially separated remote station for individual data types (e.g., medical, patient-specific and/or treatment-related data; module updates).

13. The method of any one of the preceding items, wherein in certain circumstances the transfer and execution of a module update is preferred to all other data transfers.
14. The method of any one of the preceding claims, wherein the module updates are divided into data packets and the maximum size of the data packets is from 100 kilobytes to 100,000 kilobytes.
15. The method of any one of the preceding items, wherein when a newer version of the module update is available, a check is first made as to whether one of the previous module updates is necessary in order for the new version of the module update to be performed, in which case an older version of the module update is then transferred and performed before transferring and performing the newer version of the module update.
16. The method of any one of the preceding items, wherein if a plurality of module updates for different modules is available, the module updates are transferred and performed consecutively and wherein a next module update is only transferred and performed when a previous module update is fully completed.
17. The method of any one of the preceding items, wherein if a plurality of module updates for different modules is available, the module updates are transferred and installed at the same time.
18. The method of any one of the preceding items, wherein if a plurality of module updates for different modules is available, the module updates are transferred and performed consecutively, a process starting with the transfer of a next module update after a transfer of a previous module update is completed and without waiting for a successful execution of the previous module update.
19. The method of any one of the preceding items, wherein the transfer of the module update is automatically interrupted by the ventilator based on a connection between the ventilator and the spatially separated remote station.
20. The method of any one of the preceding items, wherein if the ventilator and the remote station are connected via a mobile radio connection (LTE, 3G, etc.) the transfer of the module update does not take place and is interrupted if a connection between the ventilator and the spatially separated remote station is switched to such a mobile radio connection.
21. A ventilation system, which system comprises at least one ventilator and a spatially separated remote station, a firmware and a software of the ventilator being divided into individual modules and separate updates are provided for each module in the form of module updates, and these module updates being transferred to the ventilator from the remote station via at least one interface of the ventilator and the module updates are performed on the ventilator.

LIST OF REFERENCE NUMERALS 1 ventilator
10 remote station
20 sensor module
30 conditioning module
40 detection module
50 control module
60 communication module
70 monitoring module
80 software module
90 memory module
201 sensor firmware
202 sensor firmware
301 processing firmware
302 processing firmware
401 detection firmware
502 control firmware
503 control firmware
601 communication firmware
603 communication firmware
603.1 data packet
603.2 data packet
603.3 data packet
603.4 data packet
604 communication firmware
701 monitoring firmware
801 software

What is claimed is:

1. A method for updating the firmware and software of a ventilator, wherein the method comprises dividing the firmware and the software of the ventilator into individual modules and separate updates are provided for each module in a form of module updates and these module updates are transferred to the ventilator from at least one remote station spatially separated from the ventilator via at least one interface of the ventilator and the module updates are performed on the ventilator.

2. The method of claim 1, wherein the module updates are each divided into data packets which are transferred to the ventilator via an interface of the ventilator and stored, and wherein after a transfer of all data packets of a module update the data packets are assembled and the respective module update is performed.

3. The method of claim 1, wherein the module updates are each divided into data packets, the data packets of a module update being stored on the ventilator even after an interruption of a transfer of the data packets.

4. The method of claim 3, wherein a transfer of the data packets is resumed after the interruption.

5. The method of claim 3, wherein the transfer of the data packets is resumed after the interruption, the transfer being restarted with a last data packet that was started but not completely transferred.

6. The method of claim 1, wherein the module updates are each divided into data packets, the data packets of a module update being stored on the ventilator until the module update has been performed or until a command to delete the data packets is issued.

7. The method of claim 1, wherein the module updates are each divided into data packets, transferred data packets of an incompletely transferred module update on the ventilator being discarded/deleted and missing data packets being not transferred if a more recent version of the module update is available.

8. The method of claim 1, wherein a message of status of the module update is generated and/or issued by the ventilator and/or the spatially separated remote station.

9. The method of claim 1, wherein transfer and/or execution of the module update is requested or confirmed on the ventilator and/or the spatially separated remote station.

10. The method of claim 1, wherein a transfer of the module update or data packets thereof is suspended under certain conditions.

11. The method of claim 1, wherein a transfer of medical, patient-specific and/or treatment-related data is prioritized over a transfer of data packets of the module updates.

12. The method of claim 1, wherein a priority of a transfer is individually adjusted on the ventilator and/or on the spatially separated remote station for individual data types.

13. The method of claim 1, wherein in certain circumstances transfer and execution of a module update is preferred to all other data transfers.

14. The method of claim 1, wherein the module updates are divided into data packets and the maximum size of the data packets is from 100 kilobytes to 100,000 kilobytes.

15. The method of claim 1, wherein when a newer version of the module update is available, a check is first made as to whether one of the previous module updates is necessary in order for the new version of the module update to be performed, in which case an older version of the module update is then transferred and performed before transferring and performing the newer version of the module update.

16. The method of claim 1, wherein if a plurality of module updates for different modules is available, the module updates are transferred and performed consecutively and wherein a next module update is only transferred and performed when a previous module update is fully completed.

17. The method of claim 1, wherein if a plurality of module updates for different modules is available, the module updates are transferred and installed at the same time.

18. The method of claim 1, wherein if a plurality of module updates for different modules is available, the module updates are transferred and performed consecutively, a process starting with the transfer of a next module update after a transfer of a previous module update is completed and without waiting for a successful execution of the previous module update.

19. The method of claim 1, wherein the transfer of the module update is automatically interrupted by the ventilator based on a connection between the ventilator and the spatially separated remote station.

20. A ventilation system, wherein the system comprises at least one ventilator and a spatially separated remote station, a firmware and a software of the ventilator being divided into individual modules and separate updates are provided for each module in a form of module updates, and these module updates being transferred to the ventilator from the remote station via at least one interface of the ventilator and the module updates are performed on the ventilator.

* * * * *